United States Patent
Wolf et al.

(10) Patent No.: US 9,730,711 B2
(45) Date of Patent: Aug. 15, 2017

(54) AIMING DEVICE FOR TARGETED DRILLING OF BONE

(71) Applicant: DePuy Synthes Products, Inc., Raynham, MA (US)

(72) Inventors: Stefan Wolf, Flumenthal (CH); This Aebi, Grenchen (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 447 days.

(21) Appl. No.: 14/103,338

(22) Filed: Dec. 11, 2013

(65) Prior Publication Data

US 2015/0157337 A1 Jun. 11, 2015

(51) Int. Cl.
*A61B 17/17* (2006.01)

(52) U.S. Cl.
CPC ...... *A61B 17/1728* (2013.01); *A61B 17/1721* (2013.01)

(58) Field of Classification Search
CPC ............................ A61B 17/17; A61B 17/1728
USPC ..................... 606/86 B, 96, 104, 280–299
See application file for complete search history.

(56) References Cited

U.S. PATENT DOCUMENTS

| | | | |
|---|---|---|---|
| 4,463,758 A | 8/1984 | Patil et al. | |
| 6,913,463 B2* | 7/2005 | Blacklock | A61B 17/176 408/115 R |
| 8,187,281 B2* | 5/2012 | Cresina | A61B 17/17 606/96 |
| 8,496,690 B2* | 7/2013 | Sixto | A61B 17/8014 606/104 |
| 2005/0182407 A1* | 8/2005 | Dalton | A61B 17/7059 606/279 |
| 2010/0256520 A1* | 10/2010 | Shabaz | A61B 17/3403 600/562 |
| 2015/0105779 A1* | 4/2015 | Smith | A61B 17/1725 606/71 |

FOREIGN PATENT DOCUMENTS

| | | |
|---|---|---|
| WO | 2007/064051 | 6/2007 |
| WO | 2011/082518 | 7/2011 |

\* cited by examiner

*Primary Examiner* — Christopher Beccia
(74) *Attorney, Agent, or Firm* — Fay Kaplun & Marcin, LLP (57) ABSTRACT

An aiming device for targeted drilling of a hole into bone includes a slot hole extending through the aiming device, the slot hole being configured to receive a guide sleeve therein at different locations therein and at different angles each of which corresponds with one of the locations along a longitudinal extension of the slot hole. The aiming device can be positioned relative to a bone plate using a positioning device including a base having a guide hole extending therethrough from a first side of the base to a second side of the base. The guide hole is formed as an elongated hole and is configured to receive the guide sleeve therein at different angles relative to the positioning device.

11 Claims, 6 Drawing Sheets

AIMING DEVICE FOR TARGETED DRILLING OF BONE

FIELD OF THE INVENTION

The present invention relates to the field of surgical instruments. In particular, the invention relates to an aiming device for targeted drilling into bone. The invention further relates to a positioning device for positioning the aiming device relative to a bone plate, and to a system for drilling into bone comprising an aiming device and a positioning device and, in particular, in combination with bone plates for the left and right femurs.

BACKGROUND

Fractures are often stabilized through the fixation of a bone plate fixed to the bone by suitable fastening elements such as, for example, bone screws, pins, etc. Holes are often drilled into the subjacent bone to facilitate the insertion of fixation elements such as bone screws, pins and other implants. To guarantee secure fixation of bone fragments to each other and of the bone plate to the bone, the fixation element must be precisely positioned in the bone. In particular, the angles at which the fixation element is inserted into the bone are of great importance. For this reason, aiming devices have been used to more accurately target the drilling of these holes. Such an aiming device may act as a drilling template aligning drill sleeves along the desired drilling paths. The aiming device comprises through holes into which for example the drill sleeves can be introduced and then a drilling instrument is guided through the drill sleeves for targeted drilling of screw holes. The drill sleeves are aligned with holes of a bone plate via an orientation of the through holes in the aiming device.

The present invention provides an improved aiming device for targeted drilling of holes into bone, and a corresponding positioning device for positioning the aiming device relative to a bone plate.

SUMMARY OF THE INVENTION

According to a first aspect of the invention, at least one slot hole extends through the aiming device between a first surface facing a bone over which a bone plate and the aiming device are positioned, and an opposing second surface facing away from the bone. The slot hole is configured to receive therein a sleeve at different locations along a longitudinal extension thereof and at different angles relative to the longitudinal extension. The inclination of the angles may increase or decrease along the longitudinal extension. In one exemplary embodiment, the slot hole possesses mutually opposing, substantially parallel surfaces.

Through the provision of a slot hole in the aiming device, it is possible to vary the angle at which a sleeve inserted through the slot hole extends through the aiming device or, more precisely, through the longitudinal extension of the slot hole. The sleeve is not fixed firmly in the slot hole, but can be shifted along the longitudinal extension of the slot hole to adjust the angle of inclination, with the angle increasing or decreasing along the longitudinal extension of the slot hole. In other words, the angle of a sleeve received in the slot hole can be increased by shifting the sleeve along the longitudinal extension of the slot hole, and may be reduced by shifting the sleeve in the opposite direction. Preferably, the angle may be increased or reduced by ±15°. This permits a user to choose, during a procedure, a desired angle at which a fixation element will be inserted into the bone.

According to an exemplary embodiment, an inner surface of the slot hole includes alignment structures that temporarily secure a sleeve received in the slot hole at any of a variety of positions each of which corresponds to a predetermined axis along which a hole may be drilled. Each of the axes passes through the slot hole at a different predetermined angle so that a user may select one of the predetermined angles corresponding to a desired path of insertion of a bone fixation element. A guide sleeve may then be fixed in the chosen position to enable reliable targeted drilling into the subjacent bone.

According to an exemplary embodiment, the alignment structure comprises a series of grooves formed in a side of the slot hole, each of the grooves extending along an axis corresponding to one the predetermined angles. Alternatively, the alignment structure may comprise a series of ribs extending into the slot hole with each of the ribs extending along an axis corresponding to one of the predetermined angles. Those skilled in the art will also understand that the alignment structure may comprise any combination of grooves and ribs desired or any other structure operable to maintain a guide sleeve inserted through the slot hole at a desired angle relative thereto. The correspondence between the individual features of the alignment structure and the desired angles of insertion through the slot hole provides a particularly precise fixation of a sleeve introduced in the slot hole. As will be described in greater detail below, the sleeve advantageously engages the alignment structure via a ratchet-like mechanism enabling movement of the sleeve through the slot hole until the sleeve reaches the desired one of the predetermined angles. The ratchet-like mechanism temporarily fixes the sleeve at the selected predetermined angle after which the sleeve may be more securely fixed in position as will be described below. Each of the individual features of the alignment structure preferably extends along a straight line parallel to one of the axes along which a hole may to be drilled. It will be appreciated an alternative alignment structure may be provided on the inner surface of the slot hole including different features or any combination of grooves, ribs and other features so long as these features permit fixation of a sleeve at any desired one of the predetermined angles within the slot hole. For example, such a structure may include knobs, arbitrary projections or recesses. In one exemplary embodiment, the shape of such these features of the alignment structure correspond to a shape of an outer surface of the sleeve.

According to one exemplary embodiment, axes of the alignment structure intersect at a common point at a selected distance from a bone-facing surface of the aiming device on the side of the bone-facing surface. Preferably, the common point is in proximity to a surface of the subjacent bone. In particular, the common point may be located in a through hole of a corresponding bone plate. This common point forms a center around which a sleeve received in the slot hole may be pivoted to vary an angle of the sleeve relative to the aiming device, and thus the introduction angle of a fixation element into the bone. While the sleeve is pivoted about the common point, it is shifted along the longitudinal extension of the slot hole, with the angle between the sleeve and the longitudinal extension of the slot hole increasing or decreasing.

According to one exemplary embodiment, the aiming device is formed mirror-symmetrically (e.g., symmetrically about a center plane extending through the aiming device parallel to and between first and second surfaces thereof). In particular, the entire aiming device may be formed mirror-symmetrically, preferably with regard to a center plane extending parallel to the first and second surfaces and dividing the aiming device between the first and second surfaces into two mirror-inverted halves. In another exemplary embodiment, only the slot hole may be formed mirror-symmetrically. Through the mirror-symmetric configuration it is possible to employ one and the same aiming device for both the right and left body halves of a patient. For example, a single aiming device may be employed with a bone plate for a patient's right proximal femur and then rotated 180 degrees for use on the left proximal femur.

According to one exemplary embodiment, the slot hole has an hourglass-like or waisted cross section in a plane perpendicular to the first and second surfaces and transverse to the longitudinal extension of the slot hole. As described above, the slot hole may be formed symmetrically. The hourglass-like waisted cross section allows a sleeve to be introduced into the slot hole at an oblique incline, in the transverse direction of the slot hole. For example, the sleeve may be introduced into the slot hole obliquely from the mutually opposing surfaces of the aiming device such that the sleeve engages a portion of the inner surface of the slot hole. In an exemplary embodiment the sleeve engages one or more surfaces of the alignment structure extending around no more than half of the circumference of the sleeve. The sleeve may engage one side of the slot hole only such as, for example, an upper region of the inner surface of the slot hole and on an opposing side of the slot hole only with a lower region of the inner surface of the slot hole. Thus, the structure may comprise on the inner surface of the slot hole two mutually independent regions for a laterally reversed application of the aiming device. The two mutually independent regions may be formed by non-contiguous portions of the inner surface of the slot hole, the first region extending from the first surface of the aiming device toward the center plane of the aiming device and the second region extending from the second surface of the aiming device toward the center plane.

A slot hole having the above-described hourglass-like cross section may, according to one exemplary embodiment, be formed by two mutually superimposed slot holes extending parallel to each other and inclined transversely to their longitudinal extension in different directions. The two mutually superimposed slot holes may be formed mirror-symmetrically with regard to a plane extending between the first and second surfaces (e.g., symmetrically about the center plane). This allows a laterally reversed employment of the aiming device, for example for employment with the left femur and alternatively with the right femur, because a sleeve can be introduced into the respective slot hole accordingly from both sides of the aiming device.

According to a further exemplary embodiment, the aiming device has a first elongate portion in which the slot hole is arranged, and a second elongate portion in which a plurality of through holes are arranged. The plurality of through holes may be substantially cylindrical and extend through the aiming device perpendicular to a longitudinal axis of the aiming device from the first to the second surface of the aiming device. The through holes may overlap one another as would be understood by those skilled in the art.

In one exemplary embodiment, the first and second elongate portions extend side by side. Each of the two elongate portions of the aiming device may extend between respective proximal and distal ends, with the proximal ends of the first and second elongate portions being interconnected to one another. The distal ends may be free (i.e., not connected to one another) or likewise interconnected. It will be appreciated that the first and second elongate portions may also be arranged side by side interconnected along all or any part of total lengths. In one exemplary embodiment, a length of the first elongate portion having the slot hole is shorter than the second elongate portion including the plurality of through holes. In another exemplary embodiment, the first and second portions may be equally long, or the second portion may be longer than the first portion. The slot hole may occupy substantially the total length of the first elongate portion. The plurality of through holes may be distributed substantially along the total length of the second elongate portion. In one exemplary embodiment the through holes may be distributed along the length of the second elongate portion at regular intervals.

In one exemplary embodiment, the first elongate portion is substantially straight while the second elongate portion extends along a curve such as an arc. The curved shape may correspond to a curve of a bone plate with which the aiming device is to be aligned, such as, for example, a bone plate for treating the human femur. In particular, it will be appreciated that the through holes may be arranged to correspond to an arrangement of through holes of the bone plate.

According to a further exemplary embodiment, the aiming device further includes at least one further through hole extending through a portion of the aiming device between the slot hole and the plurality of through holes. The at least one further through hole extends along a hole axis extending through the aiming device obliquely with regard to the first and second surfaces of the aiming device. In particular in the event that the aiming device is intended for employment with a bone plate for the human proximal femur, the at least one further through hole may be arranged in a proximal portion of the aiming device to guide bone screws into the femoral neck or, where applicable, to guide periprosthetic bone screws.

According to a further aspect of the invention, a positioning device is provided for positioning the aiming device relative to a bone plate. A base of the positioning device has a first side and an opposing second side. The surface of the first side is shaped to be adjoined to a bone plate and may, for this purpose, be non-planar, curved, bulged or wavy as would be understood by those skilled in the art. On the opposing second side, i.e., on a base side facing away from the bone, the aiming device may be coupled thereto. The base includes a guide hole extending therethrough from the first to the second side, formed as a slot hole and configured to receive a sleeve, namely the sleeve inserted through the slot hole of the aiming device, at different angles. The term "slot hole," as used herein, refers to an elongated hole having a longitudinal extension greater than its transverse extension. In other words, the guide hole does not have a circular cross section and is not cylindrical.

According to an exemplary embodiment, the guide hole tapers in the direction of the first side of the base facing the bone plate. The guide hole may be, for example, funnel shaped. This shape allows a sleeve introduced into the guide hole to be, for example, pivoted within the guide hole to be positioned at a desired angle with respect to the positioning device.

According to one exemplary embodiment, the guide hole in the base of the positioning device has at least one planar inner wall. Preferably, the guide hole will have two mutually opposing planar inner walls parallel to each other. A sleeve received in the guide hole, which can serve e.g. as a guide sleeve for a drill or for a drill sleeve, may thus be guided through the guide hole along the one planar inner wall or the two planar inner walls in a defined plane. The longitudinal extension of the slot hole of the aiming device may also extend in this plane when it is connected to the positioning device.

According to one exemplary embodiment, the positioning device includes a leg extending away from the base on the second side. An aiming device coupling is formed on the leg, preferably on its free end. A length of the leg corresponds to a distance between the aiming device and the positioning device, facilitating the alignment of the guide sleeve at a particular desired angle with respect to the aiming device.

A further exemplary embodiment includes a fastening element protruding from the base of the positioning device on the first side. The fastening element is rotatable relative to the base to fasten the positioning device to a bone plate. The fastening element may be, for example, a screw, such as a knurled-head screw, which may be screwed into a correspondingly threaded hole in the bone plate. However, other fastening elements may also be provided such as, for example, a bayonet lock or the like. In one exemplary embodiment, the positioning device may be releasably coupleable to the bone plate so that the positioning device may be removed after fixation of the bone plate on the bone.

A further aspect of the invention provides a system for drilling a hole into bone having an aiming device and a positioning device as described above. The system according to an exemplary embodiment comprises the above-mentioned sleeve which preferably possesses a cylindrical outer circumference. The cylindrical sleeve serves as a guide sleeve for a drill or for other tools, e.g. for a drill sleeve. The sleeve is adapted to extend through the slot hole of the aiming device and the guide hole of the positioning device to engage the slot hole and the guide hole. The sleeve may be positioned within the slot hole at any of a variety of predetermined angles relative to the longitudinal extension of the slot hole of the aiming device and to the positioning device. In one exemplary embodiment, the sleeve may be a slotted sleeve—e.g., the sleeve possesses at least one slot in the longitudinal direction of the sleeve, the slot preferably extending substantially parallel to a longitudinal axis of the sleeve—so that the sleeve is radially compressible.

According to a further exemplary embodiment, the system further comprises a drill sleeve which serves e.g. to guide a drill or other tool, the drill sleeve having an outer diameter corresponding to an inner diameter of the slotted sleeve so that the drill sleeve may be inserted into the slotted sleeve. The angle of the slotted sleeve relative to the longitudinal extension of the slot hole of the aiming device is variable when the slotted sleeve is compressed radially, and fixed when the drill sleeve has been inserted into the slotted sleeve. Since the outer diameter of the drill sleeve corresponds to the inner diameter of the slotted sleeve when the slotted sleeve is not in a compressed configuration, introduction of the drill sleeve into the slotted sleeve prevents the slotted sleeve from being compressed and fixes the slotted sleeve in a desired position within the slot hole. For this purpose, the outer diameter of the slotted sleeve is accordingly adapted to the slot hole. Upon a shift of the slotted sleeve within the slot hole along the longitudinal extension of the slot hole, a ratchet operation may be performed by the aligning structure on the inner surface of the slot hole. As soon as the drill sleeve has been introduced into the slotted guide sleeve, radial compression of the guide sleeve is prevented to the extent that the guide sleeve engages the aligning structure on the inner surface of the slot hole such that the slotted guide sleeve is fixed in the slot hole at a predetermined angle. Secure fixation of the slotted sleeve in the slot hole can thus be created in a simple manner without any further fastening elements, with the angular position being predetermined by the aligning structure of the inner surface of the slot hole, in particular, by grooves and/or ribs formed therein.

According to a further exemplary embodiment, the positioning device has an aiming device coupling, and the aiming device includes a positioning device coupling, which have mutually complementary surfaces. The aiming device coupling and the positioning device coupling may be configured to enable mounting of the aiming device on the positioning device in only one orientation to prevent incorrect coupling. For example, the positioning device coupling may have a coupling axis, with at least one of the positioning device coupling and the aiming device coupling being asymmetrical with regard to a plane through the coupling axis so that upon employment of the system for one of the left and right body halves of a patient, only one respective correct orientation of the aiming device can be obtained. However, identical coupling structures may be provided on the sides of the first and second surfaces of the aiming device, so that the same aiming device may be employed with a corresponding positioning device for different bone plates, e.g. for the left femur and the right femur.

According to a further exemplary embodiment, the system provides two positioning devices mirror-inverted relative to each other (e.g., mirror images of one another), to enable the fastening of the aiming device to a bone plate for the right proximal femur by means of the one positioning device and for the left proximal femur by means of the mirror-inverted positioning device. The aiming device is preferably mirror-symmetric, as described above, and may be employed with both positioning devices by simply turning the aiming device around (e.g., rotating the aiming device approximately 180° about the longitudinal axis thereof), when it is to be used for the patient's other body half. The aiming device and the two positioning devices may be supplied in a kit, which may also comprise the slotted guide sleeve and one or a plurality of different drill sleeves.

BRIEF DESCRIPTION

The preceding summary of the invention as well as the following description of an exemplary embodiment will become more easily understandable in the light of the attached drawings. An exemplary embodiment of the invention will be described hereinafter with reference to the accompanying drawings. It will be appreciated, however, that the application is not limited to the exemplary embodiment shown. The drawings show.

DETAILED DESCRIPTION

The present invention may be further understood with reference to the following description and the appended drawings, wherein like elements are referred to with the same reference numerals. The exemplary embodiments relate to an aiming device for a targeted drilling of a hole into a bone. The exemplary embodiments also relate to a positioning device for positioning the aiming device in a desired position relative to a bone plate. Although the exemplary embodiments describe an aiming device and positioning device for the targeted drilling of a hole into a proximal femur, it will be understood by those of skill in the art that the aiming device and positioning device of the present invention may be similarly utilized for the targeted drilling of any long bone.

Figure 1:
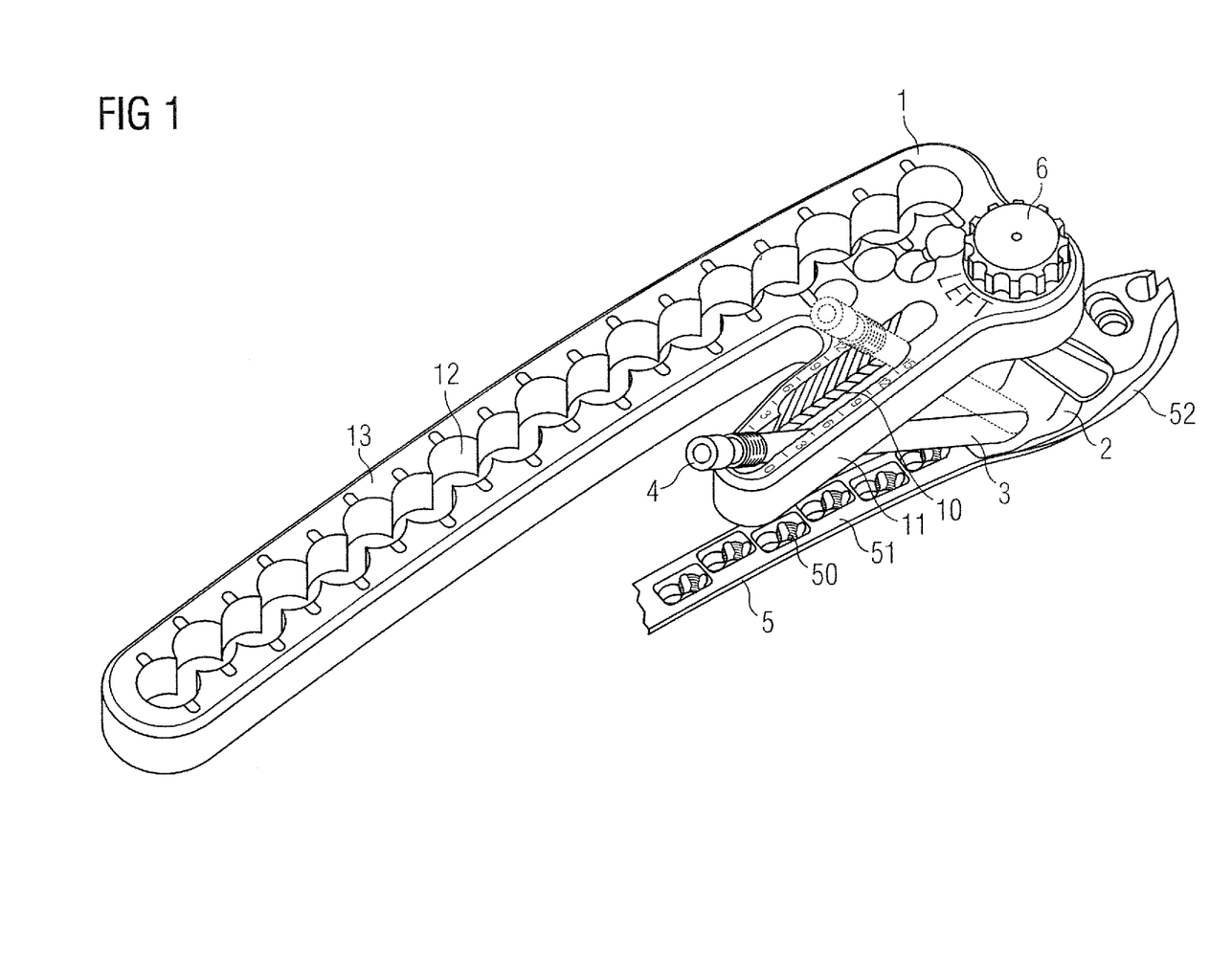
FIG. 1 shows a perspective view of an aiming device which is mounted on a bone plate by means of a positioning device, according to an exemplary embodiment of the present invention.
Figure 2:
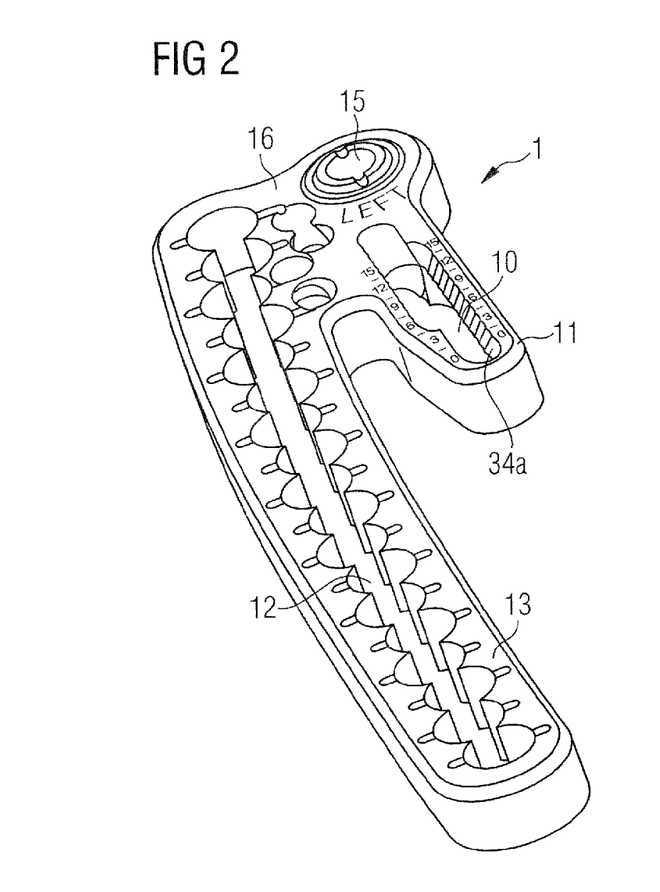
FIG. 2 shows a perspective view of the aiming device of FIG. 1.
Figure 3:
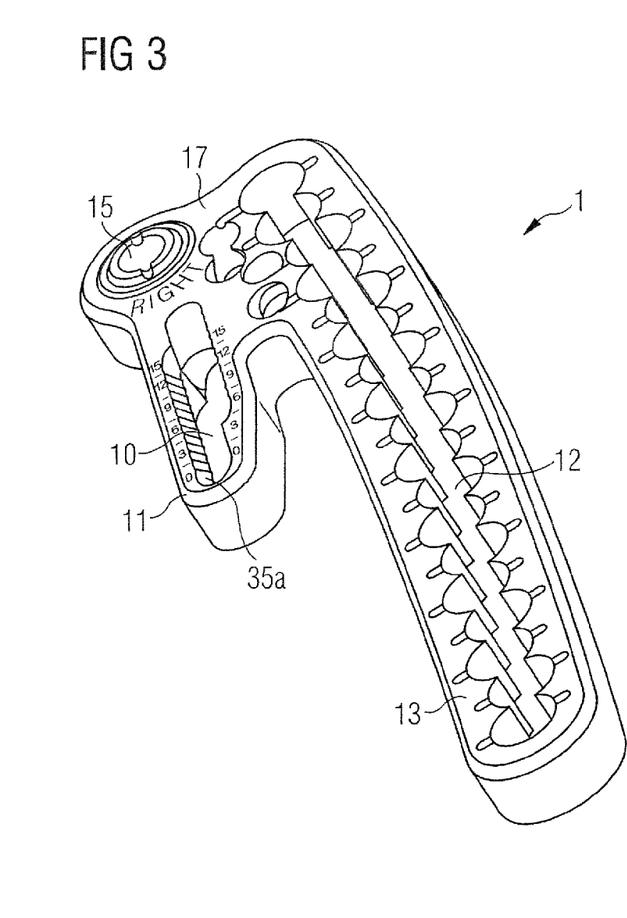
FIG. 3 shows another perspective view of the aiming device of FIG. 1.
Figure 4:
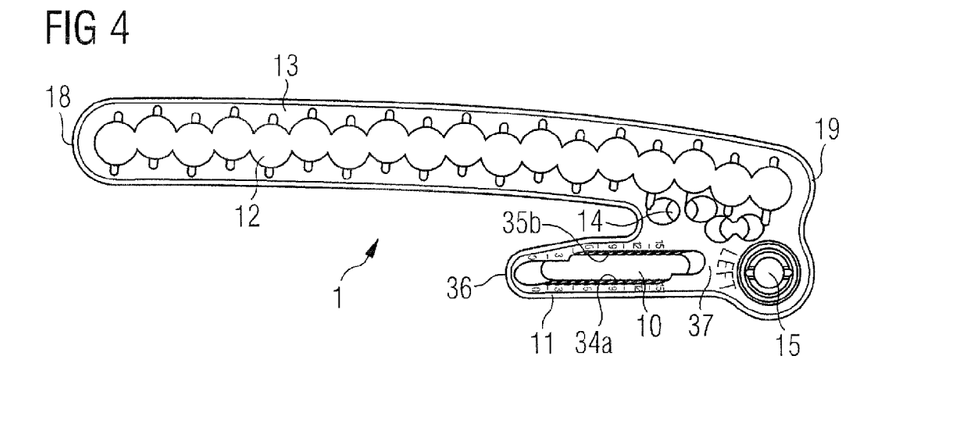
FIG. 4 shows a top plan view of the aiming device of FIG. 1.
Figure 5:
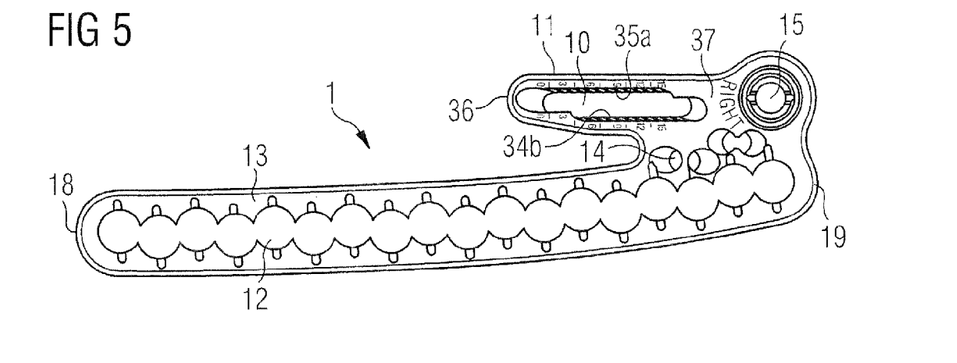
FIG. 5 shows a bottom plan view of the aiming device of FIG. 1.

As shown in FIG. 1, an aiming device 1 may be mounted on a bone plate 5 by means of a positioning device 2. The aiming device 1 is aligned with the bone plate 5 in a predetermined configuration via the positioning device 2, so that the aiming device 1 can be employed for targeted drilling of holes into a bone over which the bone plate 5 is positioned. A cylindrical guide sleeve 3 may be inserted into a slot hole 10 of the aiming device 1 to guide a drill sleeve 4 therethrough. The angle of the guide sleeve 3, and thereby the drill sleeve 4, relative to the aiming device 1 and the positioning device 2 may be adjusted. A fastening element 6 such as, for example, a knurled-head screw, may be used to fix the aiming device 1 relative to the positioning device 2.

The bone plate 5 (only partially shown) may be a bone plate for a patient's left proximal femur. As will be described in further detail below, the same aiming device 1 may also be utilized with a bone plate for a patient's right proximal femur by using a positioning device 2' configured for the right proximal femur. The bone plate 5 comprises a head portion 52 at a proximal end of the bone plate 5 as well as a shaft portion 51 extending therefrom in the direction of a distal end of the bone plate 5. The head portion 52 as well as the shaft portion 51 have through holes extending therethrough for receiving fixation elements such as bone screws with which the bone plate 5 may be fixed over the bone. The through holes 50 in the shaft portion 51 of the bone plate 5 may be formed as, for example, combination holes which have a compression portion and a variable-angle locking portion. The through holes in the proximal head portion 52 are hidden by the positioning device 2 in FIG. 1.

As shown in FIGS. 2-7, the aiming device 1 may be configured as an aiming arm which, in an exemplary embodiment, includes a first elongate portion 11 and a second elongate portion 13. The aiming device 1 further includes a first surface 16 and a second surface 17, with either the surface 16 or the surface 17 facing the subjacent bone depending on the application. The first elongate portion 11 includes a slot hole 10 extending therethrough from the first surface 16 to the second surface 17 for receiving the guide sleeve 3 with the drill sleeve 4. The second elongate portion 13 includes a plurality of substantially cylindrical through holes 12 extending therethrough from the first surface 16 to the second surface 17. When the aiming device 1 is mounted to the bone plate 5, the cylindrical through holes 12 are aligned with the through holes 50 of the shaft portion 51 of the bone plate 5 so that a drill sleeve inserted through the through holes 12 may be used to drill a hole into the bone in alignment with the through holes 50 of the bone plate 5. The aiming device 1 may further include a positioning device coupling 15 for connecting the aiming device 1 to a positioning device 2, as will be described in greater detail below.

As shown in FIG. 1 via a dashed representation of a guide sleeve, the guide sleeve 3 may be received in the slot hole 10 of the aiming device 1 at a plurality of discrete angles relative to the aiming device 1. As the guide sleeve 4 is inserted into the slot hole 10, the guide sleeve 3 is passed through a guide hole 22 (see FIG. 10) of the positioning device 2, which is also formed as a slot hole, so that the guide sleeve 3 may be moved within the guide hole 22. In an exemplary embodiment, the guide sleeve 3 may be used for the targeted drilling of a hole for a calcar screw to be introduced into the calcar femorale of a femur.

As shown in FIGS. 2-5, the slot hole 10 may be defined via alignment structures 34, 35 extending along an inner surface thereof. The alignment structures 34, 35 may be formed along, for example, opposing inner surfaces, respectively, of the slot hole 10. Preferably, the alignment structures 34, 35 comprise grooves or ribs extending into the slot hole 10 along axes extending in the direction of predetermined angles along which the guide sleeve 3 is to be aligned. In a further exemplary embodiment, the axes of each of the alignment structures 34, 35 intersect at a common point located at a distance from the aiming device 1 on the side of the surface 17 or of the surface 16 facing the bone. In particular, the common point may be located, when the aiming device 1 is mounted to the bone plate 5, near the bone surface under the guide hole 22 or in the guide hole 22 of the positioning device 2. Where the axes of the alignment structures 34, 35 intersect at a common point, a guide sleeve 3 inserted into the slot hole 10 may be moved along the longitudinal extension of the slot hole 10 by pivoting the guide sleeve about the common point. The axes of the alignment structures 34, 35, however, are not required to intersect at a common point. Axes of the alignment structures 34, 35 extend along the inner surface of the slot hole 10 to correspond to a desired direction of the guide sleeve 3 to be received in the slot hole 10 and the guide hole 22.

Figure 6:
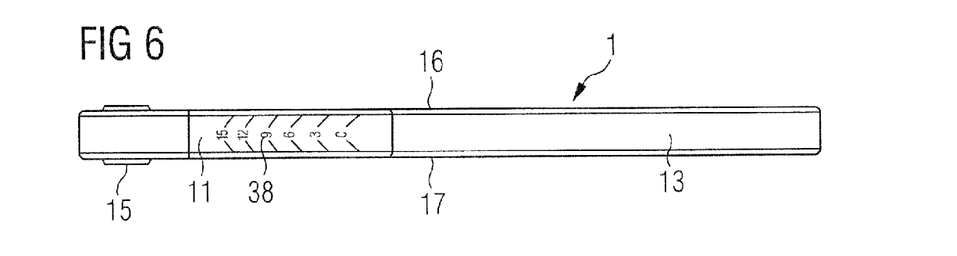
FIG. 6 shows a side view of the aiming device of FIG. 1.
Figure 7:
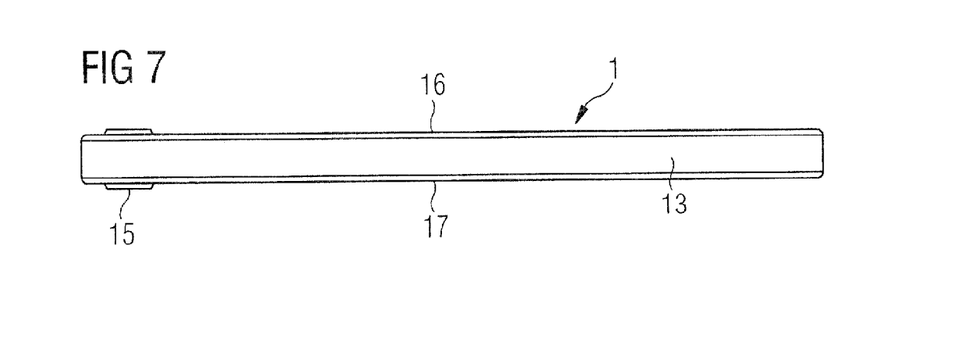
FIG. 7 shows another side view of the aiming device of FIG. 1.
Figures 16, 17:
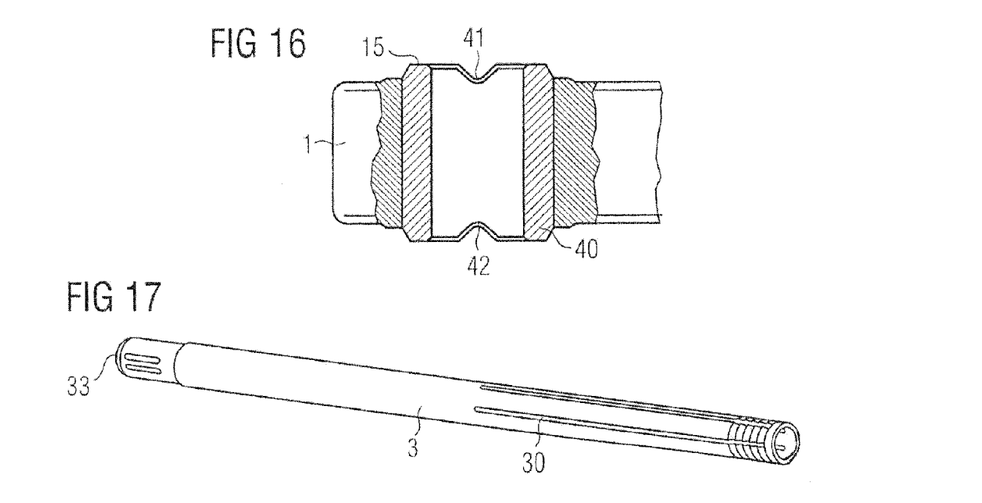
FIG. 16 shows a cross-sectional view of the positioning device coupling of the aiming device of FIG. 1.
FIG. 17 shows a perspective view of the slotted guide sleeve of FIG. 1.

The guide sleeve 3 is sized and shaped to form a ratchet mechanism together with the alignment structures 34, 35 on the inner surface of the slot hole 10. The guide sleeve 3 snaps into place at any of the predetermined angles relative to the aiming device 1 defined by the alignment structures 34, 35. As shown in FIG. 17, the guide sleeve 3 includes axial slots 30 making the guide sleeve 3 radially compressible so that the guide sleeve 3 may be compressed as it passes between projections of the alignment structures 34, 35 and then expands to snap into place within expanded portions of the slot hole 10 corresponding to each of the desired angles so that the guide sleeve 3 moves between and is held discrete positions within the slot hole 10 in a ratchet-like manner. A distal end 33 of the guide sleeve 3 is passed through the slot hole 10 and into the guide hole 22 of the positioning device 2, so that the slots 30 are positioned in the region of the slot hole 10 of the aiming device 1. A surgeon or other user may then shift the guide sleeve 3 within the slot hole 10 in the manner of a ratchet. An outer diameter of the drill sleeve 4 is selected to conform to an expanded inner diameter of the guide sleeve 3 so that, when the drill sleeve 4 is introduced into the guide sleeve 3, the guide sleeve 3 is fixed in the slot hole 10 at a desired location and angle as the guide sleeve 3 can no longer be radially compressed to move between projections of the alignment structures 34, 35. As shown in FIG. 6, and indicated by a scale 38, the angle between the guide sleeve 3 and the longitudinal extension of the slot hole 10 may be varied by up to 15°. It will be understood by those of skill in the art, however, that the slot hole 10 may also have a greater angle variability of up to 20° or up to 25° or even up to 30°, with the stated angles preferably beginning at 0° with respect to a vertical axis extending perpendicularly relative to the two aiming device surfaces 16, 17 but, where applicable, also at a negative angle, e.g. −5° or −10°.

As is evident from FIGS. 2 to 7, the aiming device 1 is may be made mirror-symmetric with regard to a center plane extending between the first surface 16 and second surface 17. In other words, the aiming device 1 is symmetrical about the center plane, which extends parallel to and between the first and second surface 16, 17. In this way, the aiming device 1 may be employed with bone plates for the left proximal femur as well as with bone plates for the right proximal femur by simply rotating the aiming device 1 180° about a longitudinal axis thereof and mounting the aiming device 1 to the bone plate using a corresponding one of the positioning devices 2, 2'. In particular, the slot hole 10 of such an embodiment is mirror-symmetrical with regard to the center plane. Thus, the slot hole 10 is formed by two superimposed slot holes, so that a guide sleeve 3 can be guided through the aiming device 1 and introduced into a corresponding guide hole 22, 22' of the positioning device 2, 2' from the first surface 16 as well as from the opposing surface 17.

Referring to FIGS. 1 to 5, the alignment structures 34, 35 on the inner surface of the slot hole 10 comprise two mutually independent regions 34a, 34b and 35a, 35b. This means that substantially only the region 34a, 34b engage a guide sleeve 3 during employment of the aiming device 1 from one side, while the guide sleeve 3 is engaged substantially only with the region 35a, 35b of the alignment structures 34, 35 upon the mirror-inverted employment of the aiming device 1. The regions 34a, 34b of the alignment structure preferably occupy substantially half of the inner surface of the slot hole 10 while the regions 34b, 35b occupy the other half. In other words, a point separating the regions 34a and 34b from the regions 35a and 35b is substantially equidistant from each of the first and second surfaces 16, 17. The region 34a, 34b comprises a portion 34a which extends from the surface 16 of the aiming device 1 in the direction of the center plane, and a portion 34b on an opposing side with regard to the transverse extension of the slot hole 10, which extends from the center plane to the surface 17 of the aiming device 1. These two portions 34a, 34b of the structure are not contiguous, but are symmetrical about the center plane such that a guide sleeve 3 received in the slot hole 10 engages the one portion 34a of the structure 34 on the one side of the slot hole 10, and the other portion 34b of the structure on the other side of the slot hole 10. The same holds for the region 35a, 35b of the structure 35 when the aiming device 1 is employed the other way round. Because the guide sleeve 3 is movable in a plane inclined with regard to the aiming device 1, it is possible to provide two mutually independent regions 34a, 34b and 35a, 35b of the structure on the inner surface of the slot hole 10 which allow the laterally reversed application of the aiming device 1. The formed slot hole 10 may thus have an hourglass-like cross section when viewed in a plane perpendicular to the surfaces 16, 17 of the aiming device 1.

As mentioned above, the aiming device 1 comprises a first elongate portion 11 and a second elongate portion 13. The first elongate portion 11 has a proximal end 37 and a distal end 36. The second elongate portion 13 has a proximal end 19 and a distal end 18. The two elongate portions 11, 13 may be interconnected at their proximal ends 37, 19. In an exemplary embodiment, the distal ends 36, 18 are free—i.e., the distal ends 36, 18 are not directly connected to one another. The two elongate portions 11, 13 may extend side by side along the longitudinal axis of the aiming device 1 and, in one exemplary embodiment, extend substantially parallel to one another along a common plane.

The aiming device 1 may further include through holes 14 extending obliquely therethrough from the first surface 16 to the second surface 17. The through holes 14 may extend through a portion of the aiming device 1 connecting the proximal ends 37, 19 of the first and second elongate portions 11, 13, respectively. The through holes 14 may be, for example, sized and shaped to receive drill sleeves for targeted drilling of holes for placing bone screws within a proximal portion of the femur, in particular, the femoral neck.

Figure 8:
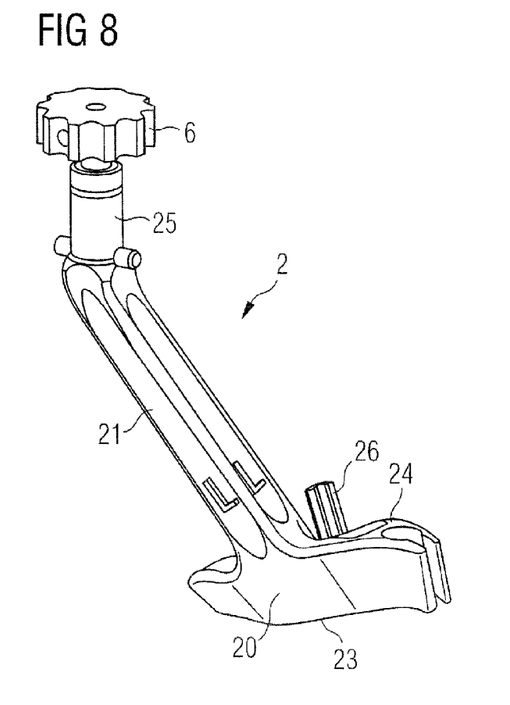
FIG. 8 shows a perspective view of the positioning device of FIG. 1.
Figure 9:
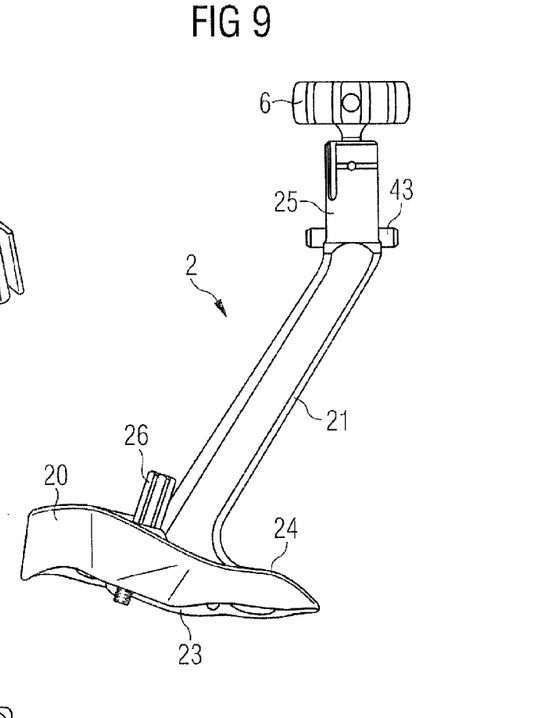
FIG. 9 shows a side view of the positioning device of FIG. 1.
Figure 10:
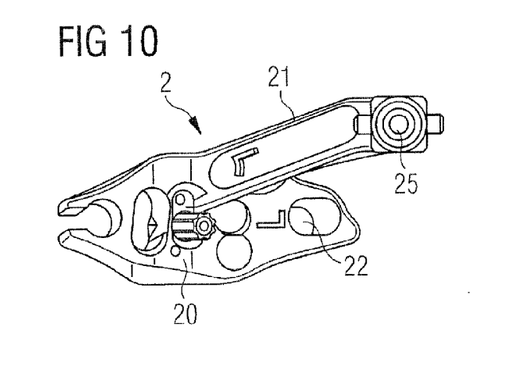
FIG. 10 shows a top plan view of the positioning device of FIG. 1.
Figure 11:
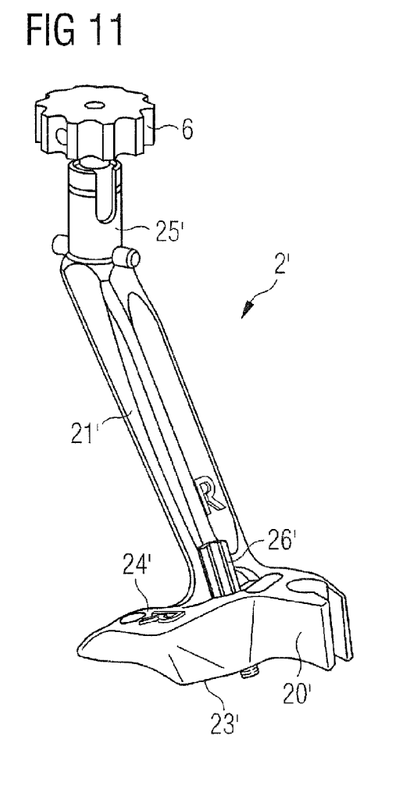
FIG. 11 shows a perspective view of a positioning device according to another exemplary embodiment of the present invention.
Figure 12:
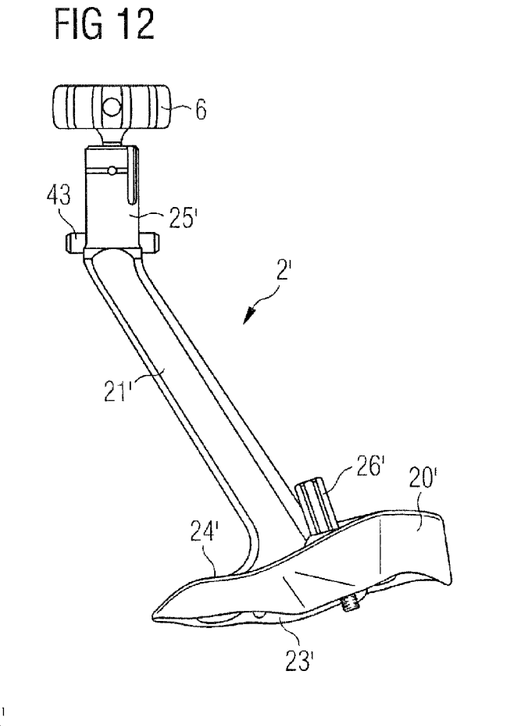
FIG. 12 shows a side view of the positioning device of FIG. 11.
Figure 13:
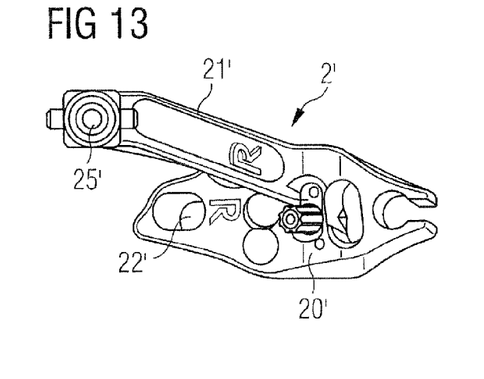
FIG. 13 shows a top plan view of the positioning device of FIG. 11.

FIGS. 8 to 10 show the positioning device 2 configured for employment with the bone plate 5 for a left proximal femur, as represented in FIG. 1. FIGS. 11 to 13 show a positioning device 2' configured for employment with a bone plate for a right proximal femur. Positioning device 2, 2' may be mirror-inverted relative to one another—e.g., mirror images of one another.

The positioning device 2 for a bone plate for the left proximal femur possesses a base 20 having a surface 23 adjoining the bone plate 5 during use and is accordingly contoured. In other words, the surface 23 is not planar, but e.g. bulged, curved or wavy in accordance with a shape of the bone plate 5. A leg 21 extends from an opposing side 24 of the base 20 and includes an aiming device coupling 25 at an end thereof. A length of the leg 21 corresponds to a desired distance of the aiming device 1 from the bone plate 5, over which distance the guide sleeve 3 extends. The positioning device 2 may be fastened to the bone plate 5 via, for example, a screw 26 which protrudes from the surface 23, to engage a correspondingly threaded hole of the bone plate 5. It will be appreciated that other fastening elements are also possible for fastening the positioning device 2 to a bone plate, such as for example a bayonet lock or the like.

As shown in FIG. 10, the guide hole 22 in the base 20 of the positioning device 2 may be formed as a slot hole. In other words, the guide hole 22 does not have a circular cross section, but is elongated along a longitudinal axis thereof—i.e., a longitudinal extension of the guide hole is greater than its transverse extension. As explained above in connection with the aiming device 1, the guide sleeve 3 is introduced with its distal end 33 into the guide hole 22 and is movable therewithin due to the shape of the guide hole 22. By moving the guide sleeve 3 within the guide hole 22, the angle between the base 20 and the guide sleeve 3 may be varied. In particular, since the guide sleeve 3 may be moved within the slot hole 10 of the aiming device 1 in a ratchet-like fashion within a plane extending substantially perpendicularly through the first and second surfaces 16, 17 and between opposing inner surfaces of the slot hole 10, the guide hole 22 has at least one, and, as in this embodiment, preferably two, planar inner walls along which the guide sleeve 3 is movable.

The same holds for the mirror-inverted positioning device 2'. The positioning device 2' for a bone plate for the right proximal femur possesses a base 20' having a surface 23' which adjoins the bone plate during use and is accordingly contoured. In other words, the surface 23' is not planar, but e.g. bulged, curved or wavy in accordance with a shape of the bone plate. A leg 21' extends from an opposing side 24' of the base 20' and includes an aiming device coupling 25' at an end thereof. A length of the leg 21' corresponds to a distance of the aiming device 1 from the bone plate 5, over which distance the guide sleeve 3 extends. The positioning device 2' may be fastened to the bone plate via, for example, a screw 26' which protrudes from the surface 23' to engage a correspondingly threaded hole of the bone plate 5. It will be appreciated that other fastening elements are also possible for fastening the positioning device 2' to a bone plate, such as for example a bayonet lock or the like.

As shown in FIG. 13, the guide hole 22' in the base 20' of the positioning device 2' may be formed as a slot hole, meaning that it does not have a circular cross section, but is an elongated hole having a longitudinal extension greater than its transverse extension. As explained above in connection with the aiming device 1, the guide sleeve 3 is introduced with its distal end 33 into the guide hole 22' and is movable therewithin due to the shape of the guide hole 22'. By moving the guide sleeve 3 within the guide hole 22', the angle between the base 20' and the guide sleeve 3 may be varied. In particular since the guide sleeve 3 through the slot hole 10 of the aiming device 1 is movable in a plane extending substantially perpendicularly relative to the first and second surfaces 16, 17 and between opposing inner surface of the slot hole 10, the guide hole 22' has again at least one planar inner wall along which the guide sleeve 3 is movable.

Figure 14A:
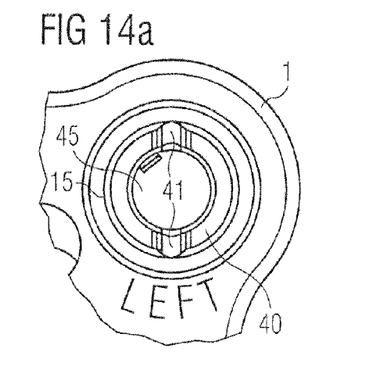
FIG. 14a shows a first plan view of a positioning device coupling of the aiming device of FIG. 1.
Figure 14B:
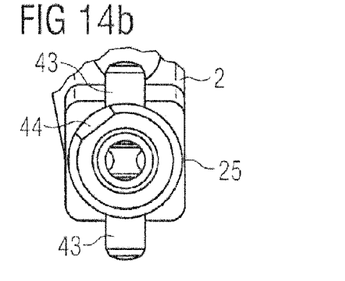
FIG. 14b shows a plan view an aiming device coupling of the positioning device of FIGS. 8-10.

FIG. 14a shows the first surface 16 of the aiming device 1 to illustrate a portion of a positioning device coupling 15 for use in, for example, a left side configuration. As shown in FIG. 14a, the aiming device 1 includes the positioning device coupling 15 which, in an exemplary embodiment, comprises an insert 40 insertable into an opening of the aiming device 1. In an exemplary embodiment, the insert 40 is formed of a metal, whereas the aiming device 1 is preferably formed of a plastic, e.g. PEEK. However, the insert 40 may also be formed through a portion of the positioning device 2 formed integrally therewith. The positioning device coupling 15 is formed such that the positioning device 2 is fixable only in a desired orientation. In particular, this prevents the aiming device 1 from being mounted on the positioning device 2' intended for a patient's right body half in an orientation intended for the left body half, and vice versa. Preferably, the positioning device coupling 15 is for this purpose asymmetric with regard to a plane through a coupling axis which, in an exemplary embodiment, extends through the insert 40 perpendicularly to the surfaces 16, 17 of the aiming device 1. For this purpose, a pin 45 or other adjusting element protrudes into the opening of the insert 40 to engage a corresponding recess 44 of an aiming device coupling 25 of the positioning device 2 and prevent an incorrect mounting. For further precise alignment of the aiming device 1 with regard to the positioning device 2, the positioning device coupling 15 comprises recesses 41 which engage a pin 43 of the aiming device coupling 25 here (see FIG. 14b). Through tightening of the knurled-head screw 6 engaging a threaded hole on the face of the aiming device coupling 25, the pin 43 is drawn into the recesses 41, and the aiming device 1 is fixed in the correct orientation. The axis of the pin 45 and the axis of the recesses 41 may be mutually offset (for example by 35°). The pin 45 preferably protrudes through the body of the aiming device 1 and through the insert 40, so that the insert 40 is secured against unintended rotation relative to the body of the aiming device 1. It will be appreciated that other configurations of the aiming device coupling 25 and of the positioning device coupling 15 are possible, so long as the coupling couplings provide the described keyed alignment.

Figure 15A:
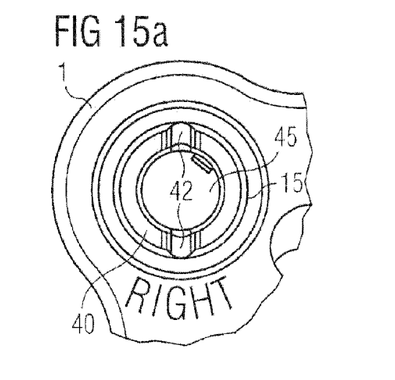
FIG. 15a shows a second plan view of the positioning device coupling of the aiming device of FIG. 1.
Figure 15B:
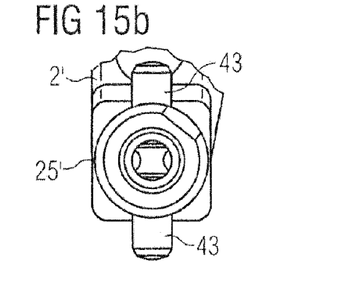
FIG. 15b shows a plan view of an aiming device coupling of the positioning device of FIGS. 11-13.

FIG. 15a shows the aiming device 1 from the opposing side 17 of the aiming device 1 to illustrate a portion of the positioning device coupling 15 for use in, for example, the right side configuration. The insert 40 has on this side, corresponding recesses 42 which engage the pin 43 of the aiming device coupling 25' of the positioning device 2' (see FIG. 15b). Otherwise, the remarks made in connection with FIGS. 14a, 14b apply accordingly.

Thus, according to one exemplary embodiment of the present invention, a system comprises a positioning device 2 for the left side and a mirror-inverted positioning device 2' for the right side, but only one aiming device 1, which is formed mirror-symmetrically (i.e., symmetrically about a center plane) to be utilized with both positioning devices 2, 2' by being rotated 180° about a longitudinal axis thereof.

Although the preferred embodiment was described with reference to a patient's left or right proximal femur, it will be understood by those of skill in the art that the principle of the invention may also be applied to aiming devices and positioning devices for other bones. For example, the described system may also be utilized for the distal femur, the tibia or other long bones. It will be appreciated that the shape and dimensioning of the aiming device and of the positioning device can be adapted in accordance with the case of application without impairing the principle of the invention.

It will be apparent to those skilled in the art that various modifications and variations may be made in the structure and the methodology of the present invention, without departing from the spirit or scope of the invention. Thus, it is intended that the present invention cover the modifications and variations of the invention provided that they come within the scope of the appended claims and their equivalents.

What is claimed is:

1. An aiming device for targeted drilling of a hole into bone, the aiming device is configured to be coupled to a bone plate, the device comprising:
   a first surface;
   an opposing second surface; and
   a slot hole extending therethrough from the first surface to the second surface, the slot hole sized and shaped to receive a sleeve therethrough at each of a plurality of locations along a longitudinal extension of the slot hole to vary an angle of the sleeve relative to the aiming device, wherein, when a sleeve is received in the slot hole, the angle of the sleeve relative to the aiming device increasing as the sleeve is moved in a first direction along the longitudinal extension and decreasing as the sleeve is moved in a second direction opposite the first direction along the longitudinal extension, wherein the slot hole includes a fixed alignment structure along an inner surface thereof fixing a sleeve received in the slot hole at each of the plurality of locations, the sleeve being fixed in each location at an angle corresponding to the location, the alignment structure including at least one alignment feature in an inner wall of the slot hole at each of the locations, each of the alignment features extending along an axis corresponding to the predetermined angle of that location, wherein axes of the alignment features intersect at a common point located near a surface of the bone and separated from the aiming device on a side of one of the first and second surfaces.

2. The aiming device according to claim 1, wherein the alignment features comprise one of grooves and ribs.

3. The aiming device according to claim 1, wherein a first angle of the sleeve relative to the aiming device in a first one of the locations within the slot hole varies by up to 15° relative to a second angle of the sleeve relative to the aiming device in a second one of the locations within the slot hole.

4. The aiming device according to claim 1, wherein the slot hole has an hourglass-like cross section in a plane perpendicular to the first and second surfaces.

5. The aiming device according to claim 1, wherein the slot hole includes two mutually superimposed slot holes extending parallel to each other and inclined transversely to their longitudinal extension in different directions.

6. The aiming device according to claim 1, further comprising a first elongate portion through which the slot hole extends and a second elongate portion through which a plurality of first through holes extend.

7. The aiming device according to claim 6, wherein the first elongate portion extends from a proximal end to a distal end and the second elongate portion extends from a proximal end to a distal end, the proximal ends of the first and second elongate portions being connected to one another.

8. The aiming device according to claim 6, wherein the first elongate portion extends along a substantially straight line.

9. The aiming device according to claim 6, wherein the second elongate portion extends arcuately.

10. The aiming device according to claim 6, comprising a further through hole extending through the aiming device from the first surface to the second surface, the further through hole being located between the slot hole and the plurality of first through holes and extending along a hole axis oblique with respect to the first and second surfaces of the aiming device.

11. The aiming device according to claim 1, wherein the aiming device is dimensioned to engage a bone plate for the human proximal femur.

* * * * *